United States Patent [19]

Samaritoni

[11] Patent Number: 4,628,088

[45] Date of Patent: Dec. 9, 1986

[54] PREPARATION OF SUBSTITUTED PYRIDAZINES

[75] Inventor: Jack G. Samaritoni, Knightstown, Ind.

[73] Assignee: Eli Lilly and Company, Indianapolis, Ind.

[21] Appl. No.: 631,654

[22] Filed: Jul. 17, 1984

[51] Int. Cl.[4] .......................................... C07D 237/12
[52] U.S. Cl. ..................................... 544/224; 544/241
[58] Field of Search ........................................ 544/224

[56] References Cited

U.S. PATENT DOCUMENTS

| | | | |
|---|---|---|---|
| 3,801,580 | 4/1974 | Minisci et al. | 260/290 |
| 3,947,437 | 3/1976 | Johnston | 544/241 |
| 4,314,844 | 2/1982 | Swithenbank | 71/92 |
| 4,508,720 | 4/1985 | Kan et al. | 514/247 |

FOREIGN PATENT DOCUMENTS 0072726  2/1983  European Pat. Off. .

OTHER PUBLICATIONS

Heinisch, G. et al., "Darstellung C-4-substituierter Pyridazine durch Homolytische Alkylierung bzw. Acylierung", *Monatshefte für Chemie*, 105(3), 648–652 (1974), See Compound 2.

Minisci F., "Novel Applications of Free-Radical Reactions in Preparative Organic Chemistry", *Synthesis*, 1, 1–24 (1973), See pp. 12–19 in particular pp. 12–14.

Minisci, F., *Topics in Current Chemistry*, 62, 18 (1976).

Minisci, F. et al., *Advances in Heterocyclic Chemistry*, 16, 128 (1974).

Bertini, F. et al., "New Processes for the Homolytic Alkylation of Protonated Heteroaromaric Basis" *La Chimica e l'Industria* (Milan), 54(5), 425–426 (1972).

Minisci, F. et al., "Nucleophilic Character of Alkyl Radicals-VI: A New Convenient Selective Alkylation of Heteroaromatic Basis", *Tetrahedron*, 27, 3575–3579 (1971) p. 3579.

Clerici, A. et al., "Nucleophilic Character of Alkyl Radicals-X: Polar and Steric Effects in the Alkylation of 3-Substituted Pyridines by t-Butyl Radical", *Tetrahedron*, 30, 4201–4203 (1974).

Minisci, F. et al., "Nucleophilic Character of Alkyl Radicals-VII. Substituent Effects on the Homolytic Alkylation of Protonated Heteroaromatic Basis with Methyl, Primary, Secondary and Tertiary Alkyl Radicals" *Tetrahedron*, 28 2403–2413 (1972).

Sakamoto, T. et al., "Studies on Pyrimidine Derivatives, XVI. Site Selectivity in the Homolytic Substitution of Simple Pyrimidines", *Chem. Pharm. Bull.*, 28(2), 571–577 (1980) pp. 572, 574.

Caronna, T. et al., "3(5)-Alkylpyrazoles", *Org. Prep. Proced. Int.*, 5(3–4), 105–107 (1973).

Yutiloz, Y. et al., "Homolytic C–Methylation of Imidazolo [4,5-c] Pyridine Derivatives", *Khim. Geterotsikl. Soedin*, 7, 993 (1977).

Fiorentino, M. et al., "Displacement of the Acyl Group in Benzothiazoles by Nucleophilic Alkyl Radicals, Homolytic Aromatic ipso-Substitution", *J. Chem. Soc., Perkin II*, 13 1679–1683 (1977).

Pellicciari, R. et al., "Adamantane Derivatives of Biological Interest", *Arzneim-Forsch*, 30(12), 2103–2105 (1980).

Jacobsen, N. et al., "Reversibility and Isotope Effects in the Homolytic Substitution of Benzoquinone and Pyridine Mechanism of Homolytic Substitution", *Acta Chem., Scand.*, B33 499–502 (1979).

Anderson, J. et al., "Silver (I)-Catalyzed Oxidative Decarboxylation of Acids by Peroxydisulfate, The Role of Silver (II)", *J. Amer., Chem. Soc.*, 92(6), 1651–1659 (1970).

Tiecco., M., "Radical Ipso Attack and Ipso Substitution in Aromatic Compounds", *Acc. Chem. Res.*, 13, 51–57 (1980) Scheme III.

Heinisch, G. et al., "Syntheses and Reactions of Pyridazine Derivatives XX Studies on the Radical Methylation of the 1,2-Diazine System", *Heterocycles*, 22(6), 1395–1402 (1984).

*Primary Examiner*—Donald G. Daus
*Assistant Examiner*—Stephen M. Kapner
*Attorney, Agent, or Firm*—Joseph A. Jones

[57] ABSTRACT

A novel process is described for preparing substituted pyridazines, where a less substituted pyridazine is reacted with a carboxylic acid in the presence of a silver ion as catalyst, using peroxydisulfate ion. The reaction is run at a temperature from about 40° to 80° C. in an aqueous solvent system and mineral acid. The substituted pyridazines are useful as intermediates to herbicidal and fungicidal compounds.

7 Claims, No Drawings

PREPARATION OF SUBSTITUTED PYRIDAZINES

BACKGROUND OF THE INVENTION

This invention belongs to the field of synthetic organic chemistry and provides a novel method of preparing substituted pyridazines. These pyridazines are useful as intermediates to herbicidal and fungicidal compounds.

The invention described herein is a homolytic alkylation process, which requires a short reaction time, but gives a high yield of substituted pyridazine. In addition, the substituted pyridazines generated in this process are made without using moisture-sensitive reagents, such as organomagnesiums and organolithiums as is characteristic of existing routes.

SUMMARY OF THE INVENTION

This invention provides a process for preparing a substituted pyridazine of the formula (I)

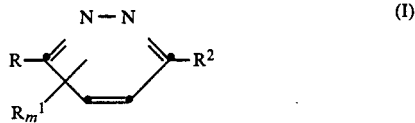

which comprises reacting a less substituted pyridazine of the formula (A)

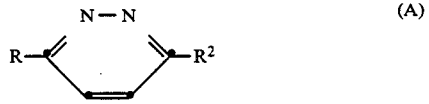

with a carboxylic acid of the formula $R^1COOH$ in the presence of peroxydisulfate ion, a catalytic amount of silver ion, and mineral acid, whose anion will not cause precipitation of the corresponding silver salt, all in an aqueous solvent system at a temperature from about 40° to about 80° C.; wherein
  R is chloride, $C_1-C_4$ alkyl, or phenyl;
  $R^1$ is $C_1-C_8$ alkyl, $C_3-C_6$ cycloalkyl, hydroxymethyl, ($C_1-C_3$ alkyl)$C_3-C_6$ cycloalkyl, ($C_1-C_6$ alkoxy)$C_1-C_8$ alkyl, adamantyl, or phenoxymethyl;
  $R^2$ is hydrogen or halo; and
  m is an integer from 1 to 2.

DETAILED DESCRIPTION OF THE INVENTION

The preferred groups in the process are those wherein
  R is chloride;
  $R^1$ is $C_1-C_4$ alkyl, $C_3-C_6$ cycloalkyl, or phenoxymethyl;
  $R^2$ is halo; and
  m is 1.

The following defines the various terms used in this application.

The term "$C_1-C_8$ alkyl" refers to the straight and branched aliphatic groups of one to eight carbon atoms including ethyl, propyl, isopropyl (1-methylethyl), butyl, methyl, isobutyl (2-methylpropyl), sec-butyl (1-methylpropyl), tert-butyl (1,1-dimethylethyl), pentyl, isopentyl (3-methylbutyl), sec-pentyl (1-methylbutyl), 1,1-dimethylpropyl, 1,2-dimethylpropyl, neopentyl (2,2-dimethylpropyl), hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, and the like. The terms "$C_1-C_4$ alkyl" "$C_1-C_3$ alkyl" are also included in this definition.

The term "$C_3-C_6$ cycloalkyl" refers to saturated aliphatic rings of three to six carbon atoms, such as cyclopropyl, cyclobutyl, cyclopentyl, and cyclohexyl.

The term "$C_1-C_6$ alkoxy" refers to the aliphatic groups of one to six carbon atoms attached to the remainder of the molecule by an oxygen atom, such as methoxy, ethoxy, propoxy, butoxy, and the like.

The halogens include bromine, chlorine, fluorine, and iodine.

The claimed process is also described in the following schematic:

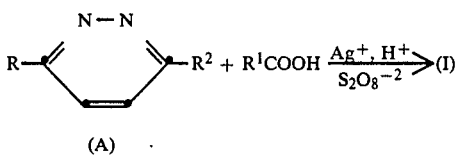

wherein R, $R^1$, and $R^2$ are defined as above.

A pyridazine of the formula (A) is reacted with a carboxylic acid of the formula $R^1COOH$. Silver (II) ion, generated from silver (I) ion and peroxydisulfate, are used in the oxidative decarboxylation of the carboxylic acid. The reaction is carried out in an aqueous solvent system with a mineral acid at a temperature from about 40° to about 80° C.

The silver ion is obtained from a water-soluble silver (I) salt, such as silver nitrate, silver fluoride, silver trifluoroacetate, silver perchlorate, and the like, with silver nitrate being preferred. The silver (I) salt is used in catalytic amounts in the reaction, but the actual catalyst generated is silver (II) ion.

Typical of the carboxylic acids of the formula $R^1COOH$ are pivalic acid (trimethylacetic acid), n-butyric acid, isobutyric acid, propanoic acid, acetic acid, cyclobutanecarboxylic acid, cyclopropanecarboxylic acid, cyclopentanecarboxylic acid, 1-adamantanecarboxylic acid, phenoxyacetic acid, glycolic acid, and the like, with pivalic acid being preferred. The source of peroxydisulfate (persulfate) ion is from an ammonium peroxydisulfate or an alkali peroxydisulfate. Ammonium peroxydisulfate is preferred.

Typical of the aqueous solvent systems that can be used are water, water-acetonitrile, and the like with water being preferred. The mineral acids that can be used must be those whose anion will not cause precipitation of the corresponding silver salt. Such mineral acids include perchloric, trifluoroacetic, sulfuric, and the like, with sulfuric being preferred.

The reaction goes rapidly and no unusual excess of reagents is necessary. In general, stoichiometric amounts of the reagents are adequate. As is usual in organic chemistry, it may be economical to use an excess of less expensive reagents to assure that more expensive reagents are fully consumed.

The amount of reactants used varies with the particular reactants, but typically 0.05 to 1.0 equivalent of silver ion; 1.0 to 5.0 equivalents of carboxylic acid; 1.0 to 3.0 equivalents of mineral acid; and 1.0 to 2.0 equivalents of peroxydisulfate ion are used with respect to the pyridazine. The preferred amounts used are 0.1 equivalent of silver and 1.0–1.75 equivalents of peroxydisulfate. The amounts of reactants used also vary with the desired amount of alkylation. In the case of dialkylation, the amount of peroxydisulfate, silver, and carboxylic acid used can be increased.

Usually the pyridazine starting material, silver salt, carboxylic acid, and mineral acid are all in an aqueous solvent system and heated to about 40° to 80° C. Maintaining the temperature, a solution of peroxydisulfate in water is added dropwise. The reaction is well stirred and heating is continued for about 1 to 2 hours. After cooling the mixture with ice-water, it is made basic in order to facilitate isolation of the product.

Preferably the reaction is heated to about 50° and then the peroxydisulfate is added. The addition of the peroxydisulfate must be at a rate to control the exotherm of the reaction. Once the addition of peroxydisulfate is complete, the reaction is stirred or agitated for about 10 minutes to 1 hour at a temperature from 70°–80° C. In order to maximize the yield of product, the temperature of the reaction must be maintained below 80°. It is also important to keep the reaction mixture well agitated. Therefore, it is advisable to use an air-driven stirrer and Morton flask for the reaction.

The products of this process are most easily isolated by using a base, such as ammonium hydroxide, sodium hydroxide, sodium carbonate, potassium carbonate, and the like, which makes the reaction solution basic. The products are then extracted with an inert organic solvent, such as methylene chloride, and the like, and dried with magnesium sulfate, sodium sulfate, and the like. The concentrated solutions are then chromatographed, if necessary, over silica gel with eluting solvents composed of mixtures of alkanes and ethers, such as hexanes and ethyl ether.

The starting materials or reagents for this process are commercially available or can be readily prepared by those skilled in the art.

The following examples are illustrative of the invention, but are not to be construed as limitations on it. All temperatures are in degrees Celsius.

EXAMPLE 1

3,6-Dichloro-4-(1,1-dimethylethyl)pyridazine

Maintaining the temperature at 70°, a solution of 2.28 grams (g) (0.01 mole, 1.0 equivalent) of ammonium peroxydisulfate in 10 milliliters (ml) of water was added dropwise with stirring over a 10-minute period to a mixture of 1.49 g (0.01 mole) of 3,6-dichloropyridazine, 0.17 g (0.001 mole, 0.1 equivalent) of silver nitrate, 3.57 g (0.035 mole, 3.5 equivalents) of pivalic acid and 2.94 g (0.03 mole, 3.0 equivalents) of sulfuric acid in 30 ml of water. After the addition was completed, the mixture was kept at 70° for an additional hour and then poured on to ice-water. The pH of the solution was adjusted to 8 with concentrated ammonium hydroxide.

After extraction with two 250-ml portions of methylene chloride, the resulting organic layers were combined, filtered, washed with 70 ml of 1N sodium hydroxide, and then dried with magnesium sulfate. Concentration afforded 1.9 g of an oil. This oil was purified over silica using a 80 to 20 ratio of hexanes to ethyl ether as the eluent.

The product weighed 1.5 g (73%) and had a melting point (MP) of 37°–40°. Nuclear magnetic resonance (NMR), infrared (IR), and mass spectra were consistent with the structure of the desired product.

The following elemental analysis was obtained: Calculated for $C_8H_{10}Cl_2N_2$: Theory: C, 46.85; H, 4.91; N, 13.66; Cl, 34.57. Found: C, 46.73; H, 5.02; N, 13.38; Cl, 34.55.

The following examples were prepared using the general procedure described in Example 1.

EXAMPLE 2

3,6-Dichloro-4-(1-methylethyl)pyridazine

Yield = 2.2 g (84%).

NMR, IR, and mass spectra were consistent with the structure of the desired product.

Molecular weight (MW) = 191.06.

Calculated for $C_7H_8Cl_2N_2$: Theory: C, 44.01; H, 4,22; N, 14.66; Cl, 37.11. Found: C, 44.02; H, 4.07; N, 14.36; Cl, 37.39.

EXAMPLE 3

3,6-Dichloro-4,5-di(1-methylethyl)pyridazine

Yield = 0.27 g (12%).

MP = 138°–141.5°.

NMR and mass spectra were consistent with the structure of the desired product.

MW = 233.14.

Calculated for $C_{10}H_{14}Cl_2N_2$: Theory: C, 51.52; H, 6.05; N, 12.02; Cl, 30.41. Found: C, 51.29; H, 5.88; N, 11.90; Cl, 30.59.

EXAMPLE 4

3,6-Dichloro-4,5-diethylpyridazine

Yield = 0.09 g (9%).

MP = 105°–110°.

NMR and mass spectra were consistent with the structure of the desired product.

MW = 205.09.

Calculated for $C_8H_{10}Cl_2N_2$: Theory: C, 46.85; H, 4.91; N, 13.66; Cl, 34.57. Found: C, 46.64; H, 4.81; N, 13.74; Cl, 34.72.

EXAMPLE 5

3,6-Dichloro-4-ethylpyridazine

Yield = 0.5 g (28%).

NMR, IR, and mass spectra were consistent with the structure of the desired product.

MW = 177.04.

Calculated for $C_6H_6Cl_2N_2$: Theory: C, 40.71; H, 3.42; N, 15.82. Found: C, 41.00; H, 3.48; N, 15.98.

EXAMPLE 6

3,6-Dichloro-4-methylpyridazine

Yield = 0.71 g (44%).

NMR and mass spectra were consistent with the structure of the desired product.

MW = 163.01.

EXAMPLE 7

3,6-Dichloro-4,5-dimethylpyridazine

Yield = 0.19 g (11%).

NMR and mass spectra were consistent with the structure of the desired product.

EXAMPLE 8

4-Cyclopropyl-3,6-dichloropyridazine

Yield = 0.59 g (31.2%).
NMR and mass spectra were consistent with the structure of the desired product.
MW = 189.05.

EXAMPLE 9

3,6-Dichloro-4,5-dicyclopropylpyridazine

Yield = 0.11 g (4.8%).
NMR and mass spectra were consistent with the structure of the desired product.

EXAMPLE 10

4-Cyclobutyl-3,6-dichloropyridazine

Yield = 1.06 g (52.4%).
NMR and mass spectra were consistent with the structure of the desired product.
MW = 203.07.

EXAMPLE 11

3,6-Dichloro-4,5-dicyclobutylpyridazine

Yield = 0.74 g (28.6%).
NMR and mass spectra were consistent with the structure of the desired product.

EXAMPLE 12

4-Cyclopentyl-3,6-dichloropyridazine

Yield = 1.66 g (76.5%).
NMR and mass spectra were consistent with the structure of the desired product.
MW = 217.10.

EXAMPLE 13

4-Cyclohexyl-3,6-dichloropyridazine

Yield = 1.15 g (50%).
MP = 72°–73.5°.
NMR, IR, and mass spectra were consistent with the structure of the desired product.
MW = 231.13.
Calculated for $C_{10}H_{12}Cl_2N_2$: Theory: C, 51.97; H, 5.23; N, 12.12; Cl, 30.68. Found: C, 52.24; H, 5.08; N, 12.24; Cl, 30.53.

EXAMPLE 14

3,6-Dichloro-4,5-dipropylpyridazine

Yield = 10.0 g (86%).
NMR spectrum was consistent with the structure of the desired product.
MW = 233.14.

EXAMPLE 15

3,6-Dichloro-4-(1,1-dimethylbutyl)pyridazine

Yield = 1.95 g (74%).
NMR, IR, and mass spectra were consistent with the structure of the desired product.
MW = 233.14.
Calculated for $C_{10}H_{14}Cl_2N_2$: Theory: C, 51.52; H, 6.05; N, 12.02; Cl, 30.41. Found: C, 51.75; H, 6.07; N, 12.02; Cl, 30.19.

EXAMPLE 16

3,6-Dichloro-4-(phenoxymethyl)pyridazine

Yield = 1.41 g (55%).
MP = 139°–142°.
NMR, IR, and mass spectra were consistent with the structure of the desired product.
MW = 255.10.
Calculated for $C_{11}H_8Cl_2N_2O$: Theory: C, 51.79; H, 3.16; N, 10.98. Found: C, 51.93; H, 2.95; N, 10.99.

EXAMPLE 17

3,6-Dichloro-4-(1-ethyl-1-methylpropyl)pyridazine

Yield = 0.63 g (<21%).
NMR spectrum was consistent with the structure of the desired product.
MW = 233.14.

EXAMPLE 18

3,6-Dichloro-4-(hydroxymethyl)pyridazine

Yield = 0.3 g (17%).
NMR spectrum was consistent with the structure of the desired product.
MW = 179.01.

EXAMPLE 19

3,6-Dichloro-4,5-dicyclopentylpyridazine

Yield = 0.24 g (8.4%).
NMR and mass spectra were consistent with the structure of the desired product.

EXAMPLE 20

3,6-Dichloro-4,5-dicyclohexylpyridazine

Yield = 0.33 g (10.5%).
NMR and mass spectra were consistent with the structure of the desired product.

The following example was prepared using the general procedure of Example 1, except 3-chloro-6-methylpyridazine was used as a starting material.

EXAMPLE 21

3-Chloro-4-(1,1-dimethylethyl)-6-methylpyridazine

Yield = 1.5 g (81%).
MP = 59°–62°.
NMR, IR, and mass spectra were consistent with the structure of the desired product.
MW = 184.67.
Calculated for $C_9H_{13}ClN_2$: Theory: C, 58.54; H, 7.10; N, 15.17; Cl, 19.20. Found: C, 55.39; H, 6.74; N, 13.98; Cl, 19.12.

The following example was prepared using the general procedure of Example 1, except 3-chloro-6-phenylpyridazine was used as a starting material and aqueous acetonitrile was used as the solvent.

EXAMPLE 22

3-Chloro-4-(1,1-dimethylethyl)-6-phenylpyridazine

Yield = 0.6 g (24%).
MP = 60°–61°.
NMR and mass spectra were consistent with the structure of the desired product.
MW = 246.74.
Calculated for $C_{14}H_{15}ClN_2$: Theory: C, 68.15; H, 6.13; N, 11.35. Found: C, 68.30; H, 6.07; N, 11.18.

The following example was prepared using the general procedure of Example 1, except aqueous acetonitrile was used as the solvent.

EXAMPLE 23

4-(1-Adamantyl)-3,6-dichloropyridazine

Yield=1.2 g (21%).
MP=172°-174°.
NMR, IR, and mass spectra were consistent with the structure of the desired product.
MW=283.
Calculated for $C_{14}H_{16}Cl_2N_2$: Theory: C, 59.38; H, 5.69; N, 9.89; Cl, 25.04. Found: C, 59.14; H, 5.58; N, 9.88; Cl, 24.82.

EXAMPLE 24

3,6-Dichloro-4-(1,1-dimethylethyl)pyridazine

A solution of 367 g (3.74 moles, 1.48 equivalents) of sulfuric acid in 1500 ml of water, 2000 ml of water, and 578 g (5.66 moles, 2.25 equivalents) of pivalic acid were added to a 12-L Morton flask charged with 375 g (2.52 moles) of 3,6-dichloropyridazine. The mixture was heated to 40° and 42.8 g (0.252 mole, 1.10 equivalent) is silver nitrate was added in one portion. After heating the mixture to 62°, a solution of 1000 g (4.38 moles, 1.74 equivalents) of peroxydisulfate in 2000 ml of water was added over a 1-hour period with constant agitation of the mixture. Heating was continued only until the temperature reached 67°. Gradually, the exotherm elevated the temperature to 82°.

After stirring an additional 10 minutes, the mixture was cooled in an ice bath to 35°. It was poured on to ice of equal volume, then with constant agitation, the solution or mixture was adjusted to a pH of 9 with concentrated ammonium hydroxide. After stirring for about 0.5 hour at 10°-15°, a precipitate was collected and then immediately dissolved in 3.5 L of ether. The solution was filtered and the filtrate was washed with three 500-ml portions of 1.0N sodium hydroxide and then 500 ml of water. It was dried with magnesium sulfate and then decolorized.

The basic washes were combined and back extracted with ether. The ethereal extract was dried with magnesium sulfate. The two ethereal extracts were concentrated in vacuo at 40°, resulting in 504 g (98.4%) of an oil. The NMR spectrum was consistent with the structure of the desired product.

One skilled in the art would also understand that compounds prepared by this invention can be used to prepare other substituted pyridazines by methods known in the art.

The compounds prepared by this process, viz., substituted pyridazines, are useful as intermediates to fungicides and to pyridazinyloxyarylureas, pyridazinylureas and pyridazinylimidazolidinones which, in turn, are useful as terrestrial herbicides. Herbicidal compounds of these types are described in U.S. Pat. Nos. 3,947,437 and 4,314,844, which are hereby incorporated by reference. The ureas and imidazolidinones can be formulated with an agriculturally-acceptable carrier and applied to the desired locus. Typical application rates are from about 0.01 to about 10 pounds. per acre (0.011 to about 11.2 kilograms per hectare).

The following preparations are offered to assure that the skilled artisan understands the preparation of the pyridazinylureas and imidazolidinones.

PREPARATION A

N'-[4-[[6-Chloro-5-(1,1-dimethylethyl)-3-pyridazinyl]oxy]phenyl]-N,N-dimethylurea A solution of 5.23 grams (g) (0.029 mole) of N'-(4-hydroxyphenyl)-N,N-dimethylurea in 125 milliliters (ml) of ethanol was added to a solution of 0.607 g (0.0264 mole) of sodium metal in 100 ml of 2B ethanol. The resulting mixture was concentrated to an oil, then diluted with benzene, and reconcentrated. The sodium salt obtained was dissolved in about 70 ml of DMSO and was added dropwise to a solution of 4.92 g (0.024 mole) of 3,6-dichloro-4-(1,1-dimethylethyl)pyridazine in 15-20 ml of DMSO. During the addition, the reaction mixture was kept between 22°-25° and was stirred for about 20 hours.

The mixture was then added dropwise to about 700 ml of ice water. After a precipitate formed, it was collected and then half of it was dissolved in 700 ml of methylene chloride. The solution was washed with 70 ml of 0.5N sodium hydroxide, dried with magnesium sulfate, and decolorized with carbon. The solution was concentrated to give 3.6 g of the title compound. After trituration in about 125 ml of ether, 2.8 g (67%) of product was collected, which had a melting point of 143°-144°.

The structure of the desired compound was confirmed by nuclear magnetic resonance and infrared spectroscopy and by mass spectrometry.

The following elemental analysis was obtained:
Calculated for $C_{17}H_{21}ClN_4O_2$: Theory: C, 58.53; H, 6.07; N, 16.06; Cl, 10.16. Found: C, 58.78; H, 6.14; N, 16.21; Cl, 10.40.

PREPARATION B

3-[6-Chloro-5-(1,1-dimethylethyl)-3-pyridazinyl]-4-hydroxy-1-methyl-2-imidazolidinone One hundred ml of 0.5N hydrochloric acid was added to 2.76 g (0.00302 mole) of N'-[6-chloro-5-(1,1-dimethyl)-3-pyridazinyl]-N-methyl-N-[2,2-(dimethoxy)ethyl]urea. The reaction mixture was heated to 55° for about 45 minutes. After cooling to 20°, a precipitate was collected and chromatographed on silica gel, using a 90/10 ratio of chloroform and ether as the eluent.

The material collected was recrystallized from a mixture of acetone and hexanes to give 1.1 g (46%) of a product with a melting point of 147°-149°. The molecular weight was 284.75. Nuclear magnetic resonance, infrared, and mass spectra were consistent with the structure of the desired product.

The following elemental analysis was obtained:
Calculated for $C_{12}H_{17}ClN_4O_2$: Theory: C, 50.62; H, 6.02; N, 19.68; O, 11.24; Cl, 12.45. Found: C, 50.65; H, 6.14; N, 19.64; O, 11.54; Cl, 12.38.

I claim:

1. A process for preparing a substituted pyridazine of the formula (I)

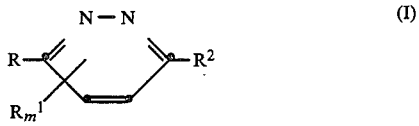

which comprises reacting a less substituted pyridazine of the formula (A)

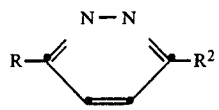

with a carboxylic acid of the formula $R^1COOH$ in the presence of peroxydisulfate ion, a catalytic amount of silver ion, and mineral acid, whose anion will not cause precipitation of the corresponding silver salt, all in an aqueous solvent system at a temperature from about 40° to about 80° C.; wherein R is chloride, $C_1$-$C_4$ alkyl, or phenyl;

$R^1$ is $C_3$-$C_6$ secondary or tertiary alkyl;

$R^2$ is halo; and m is 1.

2. The process of claim 1 wherein R is chloride.

3. The process of claim 2 wherein 1 equivalent of the pyridazine of the formula (A), 0.05–1.0 equivalent of silver ion, 1.0–5.0 equivalents of carboxylic acid, 1.0–3.0 equivalents of mineral acid, and 1.0–2.0 equivalents of peroxydisulfate ion are used.

4. The process of claim 3 wherein 0.1 equivalent of silver ion and 1–1.75 equivalents of peroxydisulfate ion are used.

5. The process of claim 4 wherein the temperature is from 50° to 70° C.

6. The process of claim 4 wherein the carboxylic acid is pivalic acid, the peroxydisulfate ion is obtained from ammonium peroxydisulfate, the silver ion is obtained from silver nitrate, the mineral acid is sulfuric acid and the aqueous solvent system is water or acetonitrile and water.

7. The process of claim 6 wherein R and $R^2$ are chloro, and $R^1$ is (1,1-dimethylethyl).

* * * * *